US010561629B2

(12) United States Patent
Kouda et al.

(10) Patent No.: US 10,561,629 B2
(45) Date of Patent: Feb. 18, 2020

(54) FOOD CONTAINING GLYCINE AND USE THEREOF

(75) Inventors: Tohru Kouda, Tokyo (JP); Chika Morishima, Tokyo (JP); Kentaro Inagawa, Kawasaki (JP); Shinobu Seki, Kawasaki (JP)

(73) Assignee: AJINOMOTO CO., INC., Tokyo (JP)

( * ) Notice: Subject to any disclaimer, the term of this patent is extended or adjusted under 35 U.S.C. 154(b) by 1618 days.

(21) Appl. No.: 11/165,200

(22) Filed: Jun. 24, 2005

(65) Prior Publication Data
US 2006/0003083 A1    Jan. 5, 2006

Related U.S. Application Data (63) Continuation-in-part of application No. PCT/JP2004/001977, filed on Dec. 24, 2004.

(30) Foreign Application Priority Data

Jan. 14, 2004    (JP) ................................. 2004-007392
May 28, 2004    (JP) ................................. 2004-158917

(51) Int. Cl.
*A61K 31/198*    (2006.01)
*A23L 33/175*    (2016.01)

(52) U.S. Cl.
CPC ................................. *A61K 31/198* (2013.01)

(58) Field of Classification Search
None
See application file for complete search history.

(56) References Cited

U.S. PATENT DOCUMENTS

| | | | |
|---|---|---|---|
| 4,397,866 A * | 8/1983 | Wurtman | 514/419 |
| 4,638,013 A * | 1/1987 | Moja et al. | 514/561 |
| 4,758,439 A | 7/1988 | Godfrey | |
| 4,980,168 A | 12/1990 | Sahley | |
| 5,112,604 A * | 5/1992 | Beaurline | A61K 31/52 424/440 |
| 5,480,865 A | 1/1996 | Kingham | |
| 5,643,954 A | 7/1997 | Komissarova et al. | |
| 6,416,795 B1 * | 7/2002 | Choi | A23F 3/34 424/725 |
| 6,461,634 B1 | 10/2002 | Marshall | |

FOREIGN PATENT DOCUMENTS

| | | |
|---|---|---|
| CN | 1078359 A | 11/1993 |
| CN | 1110112 A | 10/1995 |
| DE | 102 21 403 A1 | 12/2003 |
| GB | 1 497 316 | 1/1978 |
| JP | 02-072853 | 3/1990 |
| JP | 04-207161 | 7/1992 |
| JP | 06-505014 | 6/1994 |
| JP | 2001-224334 | 8/2001 |
| JP | 2003-116504 | 4/2003 |
| RU | 2 220 712 | 1/2004 |
| WO | WO 2004/100989 | 11/2004 |
| WO | WO 2004/103383 A1 | 12/2004 |

OTHER PUBLICATIONS

Insomnia Tip #5, Drink Warm Milk, www.well.com/~mick/insomnia/insomnia.5.html, copyright 1996 (and earlier) by Mick Winter.*
Payne-Botha, S. and Bigwood, E.J.; "Amino Acid Content of raw and heat sterilized cow's milk" Nutr. 13,4, p. 385-389, 1959.*
Buysse,D.J., Reynolds,C.F., Monk,T.H., Berman,S.R., & Kupfer,D.J. (1989). The Pittsburgh Sleep Quality Index (PSQI): A new instrument for psychiatric research and practice. Psychiatry Research, 28(2), 193-213.*
Blum et al., "Synergy of Ethanol and Putative Nerotransmitters: Glycine and Serine", Science, 176(4032), p. 292-294, 1972.*
Kryger et al., "Stress-Related Transient Insomnia," Principles and Practice of Sleep Medicine, 3rd ed., Saunders, 2000, pp. 627-628; copied provided by Applicant on Mar. 8, 2010.*
Carrier et al. J Sleep Res 6, p. 230-237, 1997.*
Sandra E. File et al, "Beneficial Effects of Glycine (Bioglycin) on Memory and Attention in Young and Middle-Aged Adults", *Journal of Clinical Psychopharmacology*, Dec. 1999, vol. 19, No. 6, pp. 506-512.
A. Eden Evins et al, "Placebo-Controlled Trial of Glycine Added to Clozapine in Schizophrenia", *American Journal of Psychiatry*, May 2000, vol. 157, No. 5, pp. 826-828.
Satoshi Terasaki, "Glycine, Its Applications and Effects", *Food Processing*, 1992, vol. 27, No. 10, pp. 11-14 (with attached English translation).
W. Yamadera et al., "Glycine ingestion improves subjective sleep quality in human volunteers, correlating with polysomnographic changes", Sleep and Biological Rhythms , vol. 5, pp. 126-131 (2007).
S. Inoue, Kyoritsu Shuppan, pp. 60-61 and 92-95 (1989) (with partial English Translation).
Goodman and Gilman, "The Pharmacological Basis of Therapeutics", pp. 354-357 (1990).
Qian Jin Lun Tan Forum, "Paradoxical Sleep and Prolonging Life", No. 9, (China Academic Journal Electronic Publishing House), Dec. 31, 2002, p. 25 (with English translation).
Herald of Medicine, "Medication of Infants' Autumn Diarrhea", No. 3, (China Academic Journal Electronic Publishing House), Dec. 31, 1997, pp. 109-110 (with English translation).
Office Action dated Jul. 13, 2012, in Japanese Patent Application No. 020227/2011 (with English-language Translation).
Pierre Maquet, "Functional Neuroanatomy of Human Rapid-Eye-Movement Sleep and Dreaming", Nature, vol. 383, pp. 163-166 (Sep. 12, 1996).

(Continued)

*Primary Examiner* — Nissa M Westerberg
(74) *Attorney, Agent, or Firm* — Oblon, McClelland, Maier & Neustadt, L.L.P.

(57) ABSTRACT

The present invention provides a food of the type based on unit of intake per serving, which contains glycine or a substance that can be hydrolyzed to give glycine in an amount of not less than 0.5 g based on glycine per serving. The food of the present invention can be applied as a food flavoring, a deep sleep disorder improving food, or a bowel movement improving food.

16 Claims, 2 Drawing Sheets

(56) References Cited

OTHER PUBLICATIONS

Seishin Igaku Jiten (Encyclopedia of Psychiatry), Kobundo, 1979; pp. 584-585, paragraph of "Sleeplessness"; pp. 351-352, paragraph of "Sleep"; and p. 353, paragraph of "Sleep Disorder", with English translation thereof.
Igaku Daijiten (Medical Dictionary), Nanzando, 6$^{th}$ Impression of the 17$^{th}$ Edition, published on Aug. 1, 1994, p. 1517, paragraph of "Non-REM Sleep"; and p. 2075, paragraph of "REM Sleep", with English translation thereof.
Billie Jay Sahley, The Anxiety Epidemic, Pain & Stress Publications, San Antonio, Texas, pp. 14, 15, 22, 23, 86 and 87 (1999).
Eric R. Braverman, The Healing Nutrients Within, 3$^{rd}$ Ed., Basic Health Publications Inc., Laguna Beach, CA, pp. 1-19 and 209-223, Chapters 1 and 14 (2003).
Nanzando, Igaku Daijiten (Medical Dictionary), 1$^{st}$ Impression of the 18$^{th}$ Edition, Published on Jan. 16, 1998, p. 1624, paragraph of "Non-REM Sleep", and pp. 2225 to2226, paragraph of "REM Sleep", with English translation thereof.
American Academy of Sleep Medicine, International Classification of Sleep Disorders, Revised: Diagnostic and Coding Manual, Chicago, Illinois: American Academy of Sleep Medicine, 2001.
Kotorii, et al., "Effect of Psychoactive Drugs on Sleep in Insomnia," Japanese Journal of Clinical Psychopharmacology (Rinsyo seisin yakuri) 14: 401-410, 2011 (with partial English-language translation).
Pagel, et al., "Medications for the Treatment of Sleep Disorders: An Overview," Primary Care Companion J. Clin. Psychiatry, 2001:3(3).
Atsuyoshi Mori, "Sleep Disturbance in the Elderly," *Japanese Journal of Geriatrics*, 27 (1), pp. 12-17 (1990) with English II Abstract and English Translation of p. 13, Figure 1, p. 16 left column, lines 3-15 and Figure 3.

\* cited by examiner

FIG. 2

FOOD CONTAINING GLYCINE AND USE THEREOF

CROSS REFERENCES TO RELATED APPLICATIONS

This application is a continuation-in-part, of International Patent Application No. PCT/JP2004/019771, filed on Dec. 24, 2004, and claims priority to Japanese Patent Application No. 2004-007392, filed on Jan. 14, 2004, and Japanese Patent Application No. and 2004-158917, filed on May 28, 2004, all of which are incorporated herein by reference in their entireties.

BACKGROUND OF THE INVENTION

Field of the Invention

The present invention relates to a food containing glycine and use thereof.

Discussion of the Background

Glycine is a non-essential amino acid having the simplest structure of $CH_2(NH_2)COOH$. Glycine is an amino acid approved as a food additive and contained in many foods. For example, beverages contain glycine at a maximum content of about 50 mg/100 ml for the preservation of quality. In addition, glycine is also contained in fish cake products such as steamed fish paste and the like. As a known function of glycine, its intake at 0.1 g per day increases memory and attention (see, File. S. E. et al., Journal of Clinical Psychopharmacology, US, 1999, vol. 19, No. 6, pp. 506-512). Furthermore, addition of glycine as an antispoilage agent for food together with maltose is known (see, JP-A-2-72853), in which case the amount of glycine to be added is, for example, about 0.3% (W/W).

SUMMARY OF THE INVENTION

Accordingly, it is one object of the present invention to provide novel glycine-containing foods of an unprecedented type, and foods having a new function based on glycine.

These and other objects, which will become apparent during the following detailed description, have been achieved by the inventors' discovery that the intake of a given amount or more of glycine can express several unconventional new functions.

Thus, the present invention provides:

(1) A food of the type based on unit of intake per serving, which contains glycine or a substance that can be hydrolyzed to give glycine, in an amount equivalent to not less than 0.5 g of glycine per serving.

(2) The food of the above-mentioned (1), wherein the content of an amino acid other than glycine or a substance that can be hydrolyzed to give an amino acid other than glycine is equivalent to not more than 5 g of an amino acid other than glycine per serving.

(3) The food of the above-mentioned (1) or (2), wherein the glycine or the substance that can be hydrolyzed to give glycine is a powder or a granule.

(4) The food of the above-mentioned (1) or (2), wherein the glycine or the substance that can be hydrolyzed to give glycine is slurry.

(5) The food of any of the above-mentioned (1)-(4), wherein the food is a beverage.

(6) The food of any of the above-mentioned (1)-(4), wherein the food is a confectionery.

(7) The food of any of the above-mentioned (1)-(4), wherein the food is a jelly, pudding or yoghurt.

(8) The food of the above-mentioned (1) or (2), which is used for masking a flavor of a food material itself or a flavor imparted by food processing.

(9) A food for improving a deep sleep disorder, which contains glycine or a substance that can be hydrolyzed to give glycine.

(10) A food for improving bowel movements, which contains glycine or a substance that can be hydrolyzed to give glycine.

(11) A method of masking a flavor of a food material itself or a flavor imparted by food processing, which comprises adding 0.15-100% by weight of glycine relative to the food as a whole.

(12) A method of improving a deep sleep disorder, which comprises taking a food containing glycine or a substance that can be hydrolyzed to give glycine.

(13) A method of improving bowel movements, which comprises taking a food containing glycine or a substance that can be hydrolyzed to give glycine.

(14) Use of a food containing glycine or a substance that can be hydrolyzed to give glycine for improving a deep sleep disorder.

(15) Use of a food containing glycine or a substance that can be hydrolyzed to give glycine for improving bowel movements.

(16) The food of the above-mentioned (9), which has a designation that the food is used for improving a deep sleep disorder.

(17) The food of the above-mentioned (10), which has a designation that the food is used for improving bowel movements.

(18) A commercial package comprising a food containing glycine or a substance that can be hydrolyzed to give glycine, and a written matter containing an explanation relating to use thereof for masking a flavor of a food material itself or a flavor imparted by food processing.

(19) A commercial package comprising a food containing glycine or a substance that can be hydrolyzed to give glycine, and a written matter containing an explanation relating to use thereof for improving a deep sleep disorder.

(20) A commercial package comprising a food containing glycine or a substance that can be hydrolyzed to give glycine, and a written matter containing an explanation relating to use thereof for improving bowel movements.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein.

DETAILED DESCRIPTION OF THE PREFERRED EMBODIMENTS

The embodiment of the present invention is described in the following.

The subject matter of the present invention relates to the novel use of glycine and a food suitable for the use thereof. As mentioned above, glycine is an amino acid having the structure of $CH_2(NH_2)COOH$. The "substance that can be hydrolyzed to give glycine" is a substance that affords glycine by hydrolysis (particularly hydrolysis in vivo). Representative examples thereof include proteins and peptides having glycine as a constituent unit. A substance that affords glycine by hydrolysis is expected to provide the same effect as that achieved by direct glycine intake, as a result of generation of glycine due to hydrolysis in the body after the intake.

The food of the type based on unit of intake per serving in the present invention contains glycine or a substance that can be hydrolyzed to give glycine in an amount equivalent to not less than 0.5 g of glycine per serving. Since such a food permits easy intake of a large amount of glycine, it allows enjoyment of effects provided by the below-mentioned novel action.

The "food of the type based on unit of intake per serving" includes foods having a predetermined amount of intake per serving. In the present specification, food is a concept broadly encompassing those that can be taken orally (excluding pharmaceutical products), and includes what is called "foods", as well as beverages, health aid foods, healthcare functional foods, supplements, and the like. The unit of intake per serving in the case of, for example, beverage, candy, chewing gum, jelly, pudding, yoghurt and the like, is a pack, a packing, a bottle and the like that define a given amount, and that in the case of a granular, powdery or slurry food is a packing and the like that define a given amount, or a container and the like that indicate the amount of intake per serving.

Being "equivalent to glycine" in relation to the content of glycine or a substance that can be hydrolyzed to give glycine in a food means that note is taken of the weight of glycine when glycine itself is contained, and when a substance that can be hydrolyzed to give glycine is contained, note is taken of the weight of glycine when the substance that can be hydrolyzed to give glycine has been entirely converted to glycine. When a food contains both glycine and a substance that can be hydrolyzed to give glycine, note is taken of the total weight of glycine and the substance that can be hydrolyzed to give glycine after complete conversion to glycine by hydrolysis.

The content of glycine or a substance that can be hydrolyzed to give glycine per serving is not less than 0.5 g, preferably not less than 1.0 g, more preferably not less than 1.5 g, when converted to the amount of glycine, in view of ease of addition to the food and the effect of the addition. In addition, the above-mentioned content is preferably not more than 100 g, more preferably not more than 60 g, from eating experience based on known findings (see, Evins A. E. et al., *American Journal of Psychiatry, US*, May 2000, vol. 157, No. 5, pp. 826-828) and ease of packing and intake.

The present inventors have also found that the presence of a large amount of one or more amino acids other than glycine in the above-mentioned food tends to prevent the benefit of the below-mentioned effects. Therefore, the total content of any amino acids other than glycine or a substance that can be hydrolyzed to give an amino acid other than glycine is preferably equivalent to not more than 5 g of the amino acids other than glycine per serving. When the total amount of any amino acids other than glycine and a substance that can be hydrolyzed to give an amino acid other than glycine exceeds 5 g in the above-mentioned food containing glycine at a lowest level permitting functional expression, the function of glycine in the present invention is suppressed.

While the lower limit of the content of any amino acids other than glycine or a substance that can be hydrolyzed to give an amino acid other than glycine is not particularly defined, for example, 50 mg per serving of an amino acid other than glycine can be mentioned, with preference given to substantial absence.

The amino acid other than glycine refers to amino acids other than the above-mentioned glycine. As used herein, by the "amino acid" is meant an organic compound having both an amino group ($-NH_2$) and a carboxyl group ($-COOH$). The "substance that can be hydrolyzed to give an amino acid other than glycine" is a substance affording an organic compound (except for glycine) having both an amino group and a carboxyl group by hydrolysis (particularly hydrolysis in vivo), and typical examples include proteins and peptides having an amino acid other than glycine as a constituent element can be mentioned.

Being "equivalent to an amino acid other than glycine" in relation to the content of an amino acid other than glycine or a substance that can be hydrolyzed to give an amino acid other than glycine in a food means that note is taken of the total of the weight of the amino acid other than glycine and the weight of the amino acid other than glycine, assuming that the substance that can be hydrolyzed to give an amino acid other than glycine has become an amino acid other than glycine by hydrolysis.

The shape or form of the glycine or a substance that can be hydrolyzed to give glycine contained in a food is not particularly limited and may be a powder or granule, as well as slurry, tablet, capsule, solution, gel, or emulsion. Of these, granules and powder are preferable for portability and ease of packing. In addition, solution, gel and slurry are also preferable because of the ease of intake.

The "slurry" glycine contained in food means a state where solid glycine is suspended in a liquid media. A part of glycine may be dissolved in the above-mentioned media.

For example, when the food is what is called a health food, not less than 0.5 g of granular glycine may be packed in an intake unit amount and the like. When the food is a healthy drink, for example, a drink containing not less than 0.5 g of glycine in a suspension or solution is placed in a bottle etc. sized for one meal or serving.

The type of food is not particularly limited and application to various foods is possible. Since glycine has a high solubility in water and has preferable sweetness, it can be suitably applied to beverages, confectioneries, jellies, puddings, and yoghurt. Beverages may be served in a bottle, a can, a paper pack and the like in the form of a solution, a suspension and the like, or may be extracted or dissolved for drinking like tea, coffee, powder beverage and the like. As used herein, by confectionery is meant favorite food taken besides meals, such as sweets and the like (e.g., candy, chewing gum, tablet and the like).

As the animals other than human to be administered to, mammals such as domestic animal, fowl and the like, experimental animals and the like can be mentioned. The mode of administration to animals other than human may be as an addition to a diet.

The invention relating to the novel use of glycine is explained in the following. The novel use of the present invention refers to the use as food flavoring, arousal during sleep and early-morning awakening suppressing food, deep sleep disorder improving food or bowel movement improving food.

Food Flavoring:

Conventionally, amino acids have been generally used as a reaction flavor under special conditions of industrial environment at high temperature. The present inventors have found that a preferable flavor can be produced upon reaction with sugars contained in the food under conditions that can be generally produced at home, such as addition of boiled water to glycine and the like. In addition, they have found that glycine can be used for masking of undesirable flavor in the food.

The food flavoring in the present invention is a concept expressing a substance that adds flavor to a food material having almost no flavor, enforcing the flavor lost during production of food, masking an unpreferable flavor which a food material itself has or which is produced during processing.

For use as a food flavoring, glycine only needs to be added to a food. The glycine content can be appropriately determined according to the amount of the flavor to be added and the level of masking to be performed. In the case of a food of the type based on the unit of intake per serving, glycine is added in an amount of preferably 0.5 to 100 g, more preferably 1.0 to 60 g, per serving. In addition, the weight of glycine in the whole food is preferably 0.15 to 100 wt %, more preferably 0.3 to 98 wt %, in consideration of solubility, preferable taste, and effectiveness of flavor and masking. A preferable mode of use for this purpose is, for example, allowing reaction with sugars by heating, such as addition of boiling water and the like. In this case, as the sugars to be reacted, sucrose, fructose, glucose, dextrin, maltose and the like can be mentioned.

The present invention also encompasses a method of masking a flavor of a food material itself or a flavor imparted by food processing, which comprises adding glycine in a proportion of 0.15 to 100% by weight, preferably 0.3 to 98 wt %, of the whole food.

The "unpreferable flavor" in a food for which glycine is used for masking includes flavors of medicinal plants used for crude drugs and Chinese herbal medicines, yacon, *Eucommia ulmoides*, and Puer contained in general health food and the like, plant extracts such as *Houttuynia cordata* used for folk remedies and the like, and herbs generally taken as herb or extracted for drinking.

Deep Sleep Disorder Improving Food:

Another aspect of the present invention is use of a food containing glycine (or a substance that can be hydrolyzed to give glycine) as a deep sleep disorder improving food.

As used herein, by the term "deep sleep disorder" is meant a condition lacking satisfaction from deep sleep on awakening, or a condition of shortage of sleep, or a condition lacking satisfaction in various aspects expected to be afforded by a suitable sleep. For example, such conditions includes shallow sleep, difficult shift to slow wave sleep indicating profound sleep after sleep onset, interrupted sleep, failure to get up at expected time and insufficient sleep hours, and is considered to often occur in an unsuitable sleep environment, in the presence of mental or physical stress, after intake of an ingredient having an awakening effect such as caffeine and the like before bedtime, at the time of excessive drinking, irregular sleep cycles and disturbed biological rhythm, as well as in a time lag environment. It is generally known that sleep plays a role of resting the body, as well as more positively relieving physical and mental fatigue, organizing the memory, and particularly in deep sleep, controlling growth and metabolism balance in the body by the secretion of growth hormone, etc. Therefore, when physical or mental conditions are not improved, fatigue remains, enthusiasm for life is diminished, oversleep occurs the next day, feel lethargic, feel shortage of sleep hours, or headaches occurs after sleeping due to a deep sleep disorder, improvement of these (improvement of deep sleep disorder) is expected to result in, for example, improved physical or mental conditions as shown by decreased lassitude, pleasant awakening on rising and the like, and realization of deep sleep, realization of fine sleep, which in turn increases willingness for life, concentration and the like. In addition, irregular work accompanying shift work and the like, jet lag and the like can also cause a deep sleep disorder, and improvement of these is expected to increase concentration during waking time, prevent oversleep during the daytime, decrease lassitude, and increase willingness to work. A deep sleep disorder improving food is effective not only for improving the above-mentioned deep sleep disorder but also allowing the inherent role of sleep to be fulfilled by improving the quality of sleep. Such a role includes, for example, affording the feeling of being refreshed on rising, decreasing lassitude, preventing tendency of oversleeping during the daytime and the like. A deep sleep disorder improving food can improve the above-mentioned deep sleep disorders. The concept represented by what is called a "sleep disorder" and "insomnia" is also included in the concept of the aforementioned "deep sleep disorder".

The food of the present invention as a deep sleep disorder improving food contains glycine or a substance that can be hydrolyzed to give glycine. The amount of intake of the aforementioned food for this purpose is preferably 0.00625 to 2.5 g/kg/day, more preferably 0.125 to 1.5 g/kg/day (daily intake per 1 kg of body weight), in an amount equivalent to glycine. The term "equivalent to glycine" has the same meaning as mentioned above. An amount not less than the lower limit of the aforementioned numerical range is sufficient to afford the aforementioned effect. When the amount of intake is increased, the intake tends to be come difficult, and the cost becomes high. A food of the aforementioned type based on the unit of intake per serving facilitates control of the amount of intake of glycine.

By the aforementioned effect relating to sleep, suppression of sleepiness during the daytime, particularly, enhanced quality of sleep in an environment associated with time difference such as jet lag and the like is expected. Life nowadays sometimes makes it difficult to ensure regular sleep because of the shift of life hours, rotation work and the like. In an environment of inconsistent life time pattern as the above, the quality of life can be improved by increasing the realization of deep sleep on waking and less sleepiness during daytime. While the effect of glycine as mentioned above is assumed to be related to several mechanisms, an action on the sympathetic and parasympathetic nervous system is considered to be particularly significant. The results in a test involving measurement of electrocardiogram of experimental animals indicate that administration of glycine dominantly acts on the parasympathetic nervous system. It is said that the present-day life tends to be sympathetic dominant due to mental stress and the like. Glycine is considered to induce shift to slow wave sleep (deep sleep), improves the quality of sleep during sleep hours, appropriately controls visceral activity during sleep and encourages natural sleep by allowing dominant action on parasympathetic that acts opposite to sympathetic dominant. When glycine is taken for such use relating to sleep, it is most suitably taken before going to bed.

As a related concept of the deep sleep disorder improving food, an arousal during sleep suppressing food and an early-morning awakening suppressing food can be mentioned. As used herein, the term "arousal during sleep" means waking up at night and being unable to go back to sleep for a while thereafter and by the "early-morning awakening" is meant waking up earlier than intended and being unable to go back to sleep again. An arousal during sleep or early-morning awakening suppressing food can improve at least one condition of the above-mentioned arousal during sleep and early-morning awakening.

The food of the present invention as an arousal during sleep or early-morning awakening suppressing food contains glycine or a substance that can be hydrolyzed to give glycine. The preferable amount of intake of the aforementioned food for this purpose is the same as that of a deep sleep disorder improving food.

Bowel Movement Improving Food:

Another embodiment of the present invention is use of a food containing glycine (or a substance that can be hydrolyzed to give glycine) as a bowel movement improving food. As used herein, by the term "bowel movement improving" is meant a food capable of improving abnormal bowel movements (i.e., constipation and diarrhea).

For use as a bowel movement improving food, a food containing glycine or a substance that can be hydrolyzed to give glycine only needs to be taken. The preferable amount of intake of the aforementioned food for this purpose is the same as that of a deep sleep disorder improving food.

Commercial Package:

In a package containing the food of the present invention and written material with an explanation relating to the use thereof, the written material is, for example, what is called a package insert describing items relating to use, efficacy, drinking/eating method and the like, and the like.

Other features of the invention will become apparent in the course of the following descriptions of exemplary embodiments which are given for illustration of the invention and are not intended to be limiting thereof.

EXAMPLES

In the tests in Experimental Examples 1-6, 8, other than the test using experimental animals, all test participants voluntarily took glycine as a food additive based on his or her independent wish as a powder or tablet or upon addition to general food, and made comments by his or her free will, which are summarized in those examples. The tests of Experimental Example 9 and the following were performed by a single-blind or double-blind placebo study upon approval of internal ethical review board and under direction of specialized physician.

Experimental Example 1

Glycine powder (substantially pure, 2 g) was added to commercially available tea bags of the blend tea shown in Table 1 and the same tea bags without the addition were also prepared. A given amount (150 ml) of hot water was added and the tea was extracted for 1 minute. Five test participants drank the extracted blend tea and commented as to the decrease of flavor by the addition of glycine as compared to non-addition of glycine. The decrease of flavor was taken as an index of the masking effect (see, Table 1). The majority of the test participants confirmed the masking effect in all three kinds of the tested blend tea, and most of them found it to be a preferable masking effect.

TABLE 1

Masking effect by addition of 2 g of glycine per serving to food (unit: person)

| | Masking effect present | | |
|---|---|---|---|
| Added to | preferable effect | unpreferable effect | No masking effect |
| Puer blend tea | 1 | 2 | 2 |
| Eucommia ulmoides blend tea | 4 | 0 | 1 |
| Korean ginseng blend tea | 3 | 0 | 2 |

Experimental Example 2

Figure 1:
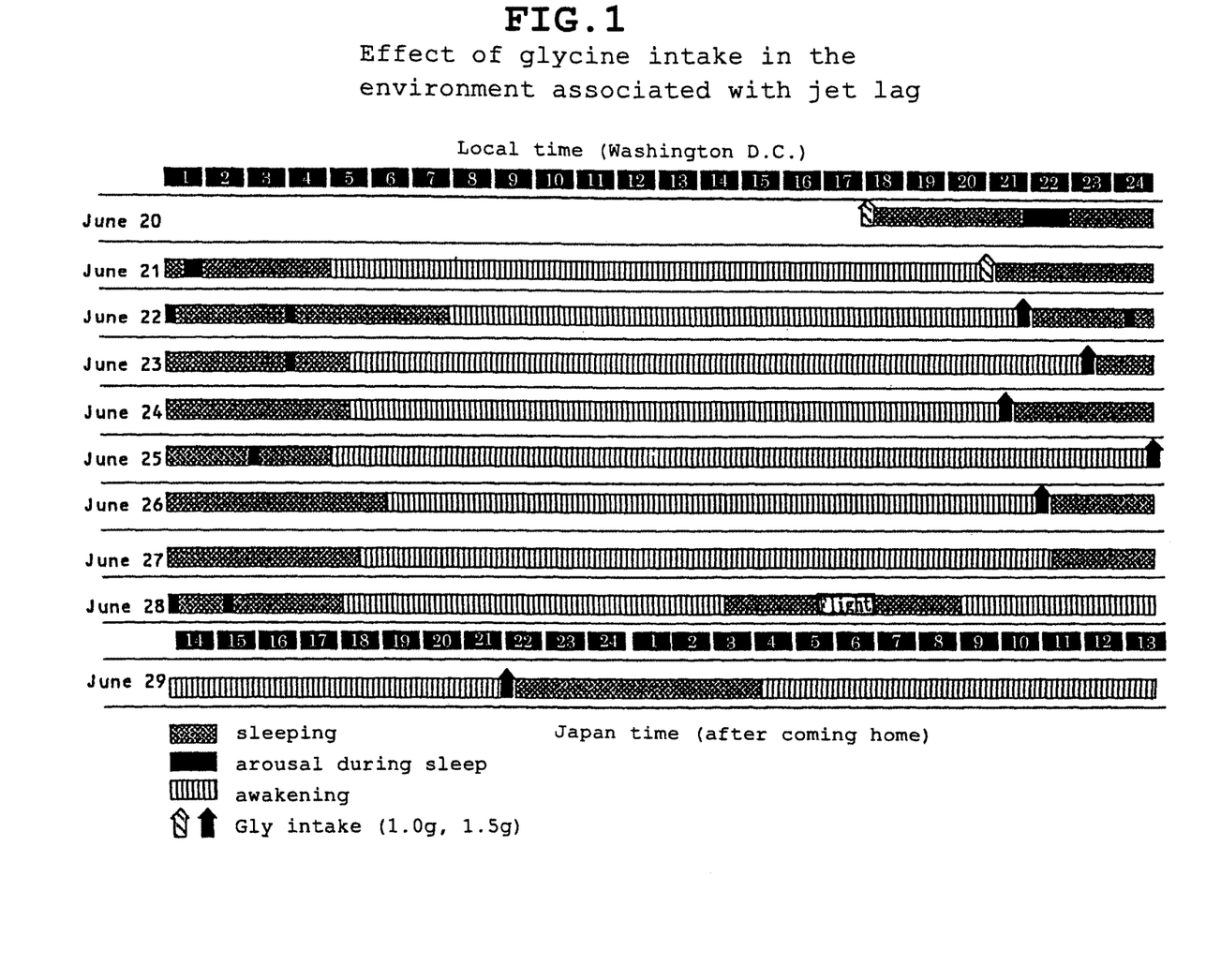
FIG. 1 is shows glycine intake and sleep hours during a trip to the East Coast, USA, by the test participant (Experimental Example 2)

The glycine intake and sleep hours when a Japanese test participant living in Japan (male, 44 years old, body weight 62 kg) traveled to the East Coast, USA, are shown in FIG. 1. In the Figure, glycine (substantially pure tablet glycine containing only excipient and flavor) was taken at the time point marked with an arrow, wherein 1.0 g was taken on "June 20" and "June 21" and 1.5 g was taken on "June 22"-"June 26" and "June 29". This test participant frequently woke up during sleep in previous similar trips, but as is clear from the results of FIG. 1, administration of glycine reduced or eliminated arousal during sleep.

Experimental Example 3

Three test participants (test participants A-C, body weight 64-74 kg) who were then visiting the U.S. for 5 days took glycine (1.5 g, substantially pure tablet glycine containing only excipient and flavor) before sleep and evaluated the sleepiness felt from 1 pm to 5 pm the next afternoon in 3 levels as compared to the absence of glycine. The results are summarized in Table 2. All three test participants felt a lower level of sleepiness during the next daytime with the intake of glycine as compared to the absence of glycine.

TABLE 2

Reduction of sleepiness during daytime the next day due to the intake of glycine in environment with time difference (unit: day)

| | | No sleepiness | Mild sleepiness | Heavy sleepiness |
|---|---|---|---|---|
| test participant A | Intake of glycine | 2 | 2 | 0 |
| | Without intake of glycine | 0 | 0 | 1 |
| test participant B | Intake of glycine | 2 | 1 | 0 |
| | Without intake of glycine | 0 | 0 | 2 |
| test participant C | Intake of glycine | 1 | 0 | 0 |
| | Without intake of glycine | 0 | 2 | 2 |

Experimental Example 4

The test participant (body weight 45 kg) took, before going to bed, 3 g of glycine directly or upon addition to various foods (see, Table 3). The content (amount based on amino acid) of an amino acid other than glycine or a substance that can be hydrolyzed to give an amino acid other than glycine in these foods was generally 0 to 4 g. As compared to free of glycine intake, easiness of falling asleep and realization of deep sleep upon waking the next morning were recorded and summarized in Table 3. By any form of glycine intake, realization of deep sleep and easiness of falling asleep were improved in most cases.

TABLE 3

Improvement of realization of deep sleep and easiness of falling asleep by glycine (3 g) intake before going to bed (unit: day)

| Food containing glycine | Days of testing | Improved realization of deep sleep | Improved easiness of falling asleep |
|---|---|---|---|
| powder | 3 | 3 | 3 |
| addition to hot milk | 4 | 4 | 4 |
| addition to yoghurt | 7 | 7 | 7 |
| addition to herb tea | 5 | 5 | 5 |
| addition to Japanese tea | 10 | 10 | 9 |
| addition to hot water or water | 14 | 14 | 14 |

Experimental Example 5

The test participants (body weight 45-80 kg) took 3 g of glycine (substantially pure glycine granule and powder) as it was, or after dissolving or suspending in water, juice, sport beverage and the like, or after addition to jelly, pudding and the like and then slept, after which they voluntarily commented on the quality of sleep as compared to the absence of intake. Out of 77 participants, 58 participants commented that the quality of sleep was improved, 2 participants commented that the quality was degraded and 17 participants commented that no effect was found. The effects on waking such as freshness on waking and improved realization of deep sleep, as well as the effect on the next day of the intake such as reduced sleepiness during daytime, and the effect after the intake such as reduced snore during sleep were found. Besides the above, the minority of participants commented that the stomach ache was reduced, fatigue did not remain the next morning, the mental stress before examination was reduced, menstrual pain became mild, oversleep ceased, stuffed nose was solved and the like (see, Table 4).

TABLE 4

Effect on quality of sleep by glycine (3 g) intake (voluntary comments of 77 participants, unit: person)

| | Enhancing effect on quality of sleep | Degrading effect |
|---|---|---|
| Awakening was fresh | 24 | 1 |
| Sleep was deeper | 10 | 0 |
| Deep sleep was realized | 8 | 0 |
| Had no dream | 4 | 0 |
| Slept well | 2 | 0 |
| Did not wake up at midnight | 6 | 1 |
| Fell asleep easily | 6 | 0 |
| sleepiness during daytime reduced | 4 | 0 |
| Snoring decreased | 19 | 0 |

Experimental Example 6

Two test participants (test participant A (body weight 52 kg), B (body weight 45 kg)) took or did not take, before going to bed, glycine (substantially pure tablet glycine containing only excipient and flavor) of the type shown in Table 5. Table 5 reports the bowel movements on the next morning and the corresponding number of days. When glycine was taken before going to bed, the bowel movements in the next morning increased. When taken together with yoghurt, the bowel movements were also improved.

TABLE 5

Improved bowel movements by glycine intake (unit: day)

| | | Presence of bowel movement | No bowel movement |
|---|---|---|---|
| test participant A | tablet intake (1 g) | 10 | 2 |
| | no intake | 4 | 6 |
| test participant B | powder intake (3 g) | 7 | 1 |
| | intake (3 g) with yoghurt | 4 | 0 |
| | only yoghurt | 3 | 2 |
| | no intake | 2 | 3 |

Experimental Example 7

Figure 2:
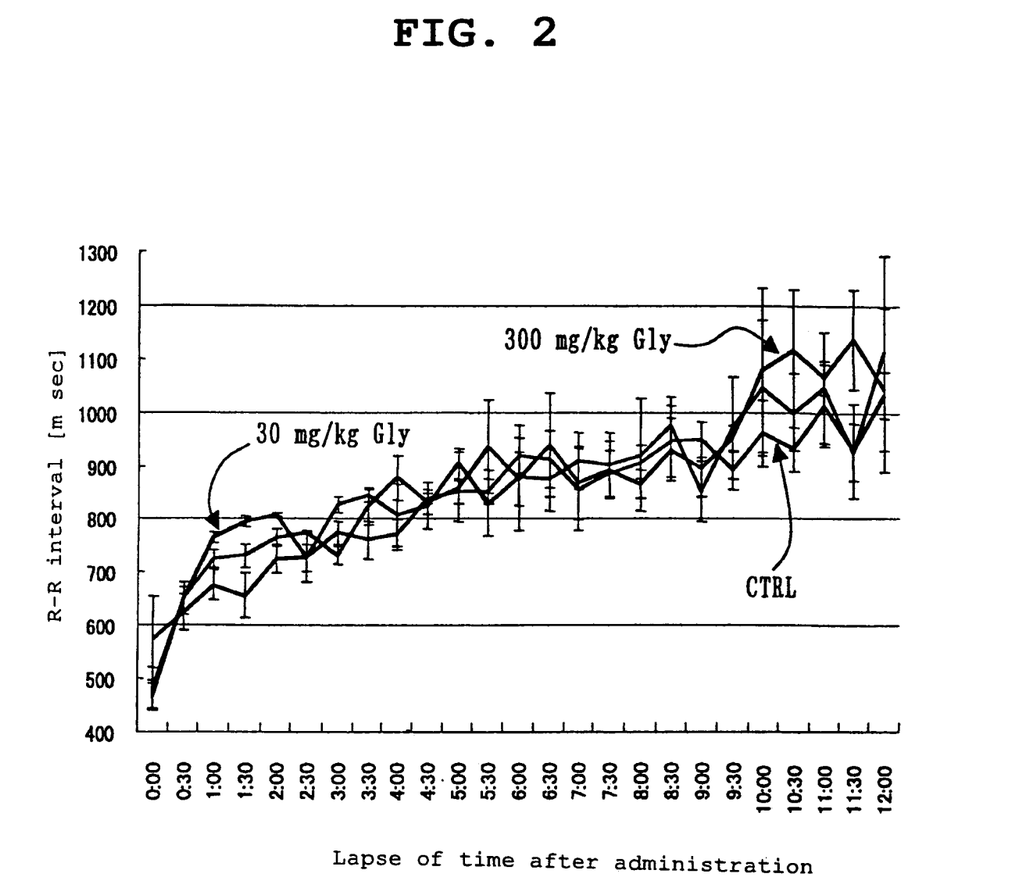
FIG. 2 is a graph showing the relationship between the lapse of time after glycine administration and R-R interval in a test using beagles (Experimental Example 7).

Glycine (substantially pure glycine powder) was administered at 0, 30, or 300 mg/kg (0 mg/kg for control, CTRL) to beagles, and using the beagles, the R-R interval in electrocardiogram was measured by a telemetry system as an index of sympathetic activity. The measurement was conducted in the night after glycine administration. From the R-R interval after oral administration of glycine, moreover, sympathetic activity ((low frequency component LF)/(high frequency component HF)) and parasympathetic activity (high frequency component HF) were examined by power spectrum analysis. FIG. 2 shows the relationship between the lapse of time after administration and the R-R interval. As a result, it was found that the R-R interval increased at 1-4 hr after administration as compared to the control, and the parasympathetic activity was dominant. The results suggest possible involvement of glycine in the relaxation of deep sleep disorders by the relative suppression of sympathetic hyperactivity.

Experimental Example 8

The test participant A (body weight 45 kg) took glycine (substantially pure powder) in an amount shown in Table 6 before going to bed by dissolving same in water, and recorded the level of realization of deep sleep. When the realization of deep sleep increased than usual, "+" was marked, when the realization of deep sleep was almost the same as usual, "±" was marked and when it became worse, "−" was marked. The results are shown in Table 6.

TABLE 6

| Amount of intake (in teaspoon) | ¼ | ½ | 1/1 |
|---|---|---|---|
| General amount (g) | 0.6 | 1.2 | 2.5 |
| Realization of deep sleep | + | + | + |

Experimental Example 9

A double-blind crossover test aiming at confirmation of the effect of glycine on sleep was performed with 15 female adults (20s-50s, body weight 46-58 kg). The test participants took glycine (granule containing citric acid and the like) in an amount equivalent to 3 g of glycine 1 hr before bedtime, and reduced maltose containing components other than glycine (citric acid and the like) and adjusted to an almost indistinguishable taste was used as a placebo. For the test, glycine and placebo were each taken for 4 days with an interval of a 3 day non-intake period, totaling 2 weeks.

(1) As a result of examination using self recording questionnaire for the evaluation of sleep condition, the test participants of 32 years old or older (6 out of 15 participants, body weight 46-58 kg) significantly showed an effect of improving physical conditions on waking (good physical shape, lethargic feeling, heavy-headed feeling and the like) and mental conditions on waking (refreshed feeling, sick feeling and the like), and the test participant having problems regarding sleep (7 out of 15 participants, body weight 46-58 kg) who marked 9 points or more in the Pittsburgh Sleep Quality Index (PSQI) significantly showed an effect of improving mental conditions on waking. The results are shown in Table 7.

TABLE 7

Improvement of physical and mental conditions on waking by glycine intake (unit: person)

| evaluation item | Comparison with placebo | 32 years old or older | PSQI not less than 9 |
|---|---|---|---|
| physical condition on waking | improved | 5 | 5 |
|  | no change | 1 | 1 |
|  | worsened | 0 | 1 |
| mental condition on waking | improved | 5 | 5 |
|  | no change | 1 | 2 |
|  | worsened | 0 | 0 |

(2) As a result of examination using self recording questionnaire for the evaluation of lassitude on waking, a tendency of reducing lassitude on waking was observed. The results are shown in Table 8. In the Table, the values of glycine and placebo show the number of test participants who showed a decrease of lassitude (decreased total point) or increase (increased total point) as compared to placebo intake, in the total point of 4 days of 10 questions (each 3 levels of 0, 1, 2 points) evaluating the lassitude on waking in a SAM lassitude check list. In the Table, the number of test participants who showed difference by 1 point or more (effective) in the total points and who showed difference by 4 points or more (remarkably effective) are shown.

TABLE 8

Effect of reducing lassitude on waking by glycine intake

|  | effective | remarkably effective |
|---|---|---|
| Reduction of lassitude (participants) | 11 | 7 |
| No change (participants) | 1 | 6 |
| Increase of lassitude (participants) | 3 | 2 |

(3) As a result of examination using self recording questionnaire for the evaluation of sleep condition, the test participants of 32 years old or older showed significant effect of improving the depth of sleep. The results are shown in Table 9. In the Table, the values of glycine and placebo show the test participant average of the points of evaluation in 8 levels in the sleep questionnaire "depth of sleep". A greater numerical value indicates that the test participant felt deeper sleep. In addition, the p value is a statistical value showing the probability when the difference between glycine and placebo was hypothesized to be null. Particularly, this value of 0.05 or below is considered to indicate a significant difference.

TABLE 9

Effect of improving depth of sleep by glycine intake

|  | glycine | placebo | P value |
|---|---|---|---|
| Sleep questionnaire "depth of sleep" | 4.88 | 4.13 | 0.042 |

(4) At the end of each 1 week test period, a question was asked about the soundness of sleep. As a result, 6 out of 15 participants answered that the week of glycine intake was fine and one participant answered that the week of placebo intake was fine. The remaining 8 participants answered that both were the same.

(5) As a result of examination using self recording questionnaire for the evaluation of sleep condition, the test participants of 32 years old or older particularly showed an effect of clearing head the next morning. The results are summarized in Table 10.

TABLE 10

Effect of clearing head the next morning by glycine intake (unit: person)

|  | Comparison with placebo | Number of participants |
|---|---|---|
| Effect of clearing head the next morning | effective | 5 |
|  | no change | 1 |
|  | worsened | 0 |

From the above, it has been shown that glycine intake affords deep sleep, and improves lassitude on waking and physical or mental condition. It is assumed that, as a result of the deep sleep, fatigue was eliminated and the condition on waking was improved.

Experimental Example 10

A double-blind crossover test aiming at confirmation of the effect of glycine on sleep was performed with 14 male adults (body weight 64-112.5 kg, average 81.2 kg) concerned about snoring and apnea condition during sleep. The test participants took glycine (granules containing citric acid and the like) in an amount equivalent to 3 g of glycine 1 hr before bedtime, and reduced maltose containing components other than glycine (citric acid and the like) and adjusted to an almost indistinguishable taste was used as a placebo.

(1) For the evaluation of sleep condition, overnight polysomnography was used for the measurement. As a result, significant difference was not observed in the time from lights-out to sleep onset, but the time from the lights-out to slow wave sleep considered to represent deep sleep was shortened and extension of the slow wave sleep in the early stage of sleep onset was confirmed.

In addition, the sleep condition of the night before was examined on waking using the sleep questionnaire. As a result, high marks were obtained for the item of "depth of sleep". This suggests that the glycine intake facilitated deep sleep. The results are summarized in Table 11. The slow wave sleep (%) in early stage of sleep onset in the Table shows a test participant average of the ratio of slow wave sleep to the early stage (1 hr) of sleep onset.

In the OSA sleep questionnaire, a test participant average of the points of 4 levels (0, 11, 21, 32 points) was calculated. A higher point value means the answer of the test participant that the sleep was deeper. The point value with the glycine intake was 16.7, which is higher than the point value 12.3 with placebo intake. This means deeper sleep afforded by the glycine intake.

TABLE 11

Effect of facilitating deep sleep by glycine intake

|  | glycine | placebo | p value |
|---|---|---|---|
| lights-out - sleep onset (min.) | 13.3 | 16.3 | 0.322 |
| lights-out - slow wave sleep (min.) | 52.2 | 103.4 | 0.042 |
| slow wave sleep (%) in sleep onset initial stage | 12.0 | 6.4 | 0.020 |

(2) The sleep condition of the night before was examined on waking using the OSA sleep questionnaire. As a result, the tendency of less time of dozing off was obtained. It is considered that resistance to sleep onset during bedtime was reduced. In the OSA sleep questionnaire, a test participant average of the points of 4 levels (0, 11, 19, 30 points) was calculated. A higher point value means the answer of the test participant that the time of dozing off was shorter. The point value with glycine intake was 24.9, which is higher than the point value 19.6 with placebo intake. This means that the time of dozing off was shorter with the glycine intake and deep sleep was obtained after the sleep onset.

Experimental Example 11

Glycine (substantially pure glycine powder) was administered to rats at 0 g/kg and 2 g/kg (0 g/kg for control) and using the rat, spontaneous electroencephalogram and cervix electromyogram were recorded through an electrode placed in the cortex hippocampus, and further, the amount of spontaneous motor activity was measured by an infrared ray monitor. The sleep-wake cycle was analyzed from the electroencephalogram, electromyogram and behavior record (kymogram), and percent occupation of light period and dark period and latency time were calculated. Table 12 shows percent occupation of sleep-wake cycle at every 3 hours, Table 13 shows latency time and Table 14 shows the amount of spontaneous motor activity at 6 hours after administration (all in mean±standard error).

TABLE 12

Percent occupation of each sleep - wake cycle (unit: %) after administration

| sleep - wake cycle | Lapse of time (hr) after administration | light period | | dark period | |
|---|---|---|---|---|---|
|  |  | control group | glycine group | control group | glycine group |
| waking stage | 0-3 | 44.4 ± 7.1 | 39.6 ± 6.0 | 71.6 ± 4.1 | 67.6 ± 7.9 |
|  | 4-6 | 32.4 ± 1.3 | 20.7 ± 0.8 | 69.3 ± 1.3 | 65.6 ± 3.4 |
| slow wave sleep stage | 0-3 | 49.6 ± 6.1 | 54.9 ± 4.9 | 25.7 ± 3.6 | 29.2 ± 6.5 |
|  | 4-6 | 56.1 ± 1.9 | 65.9 ± 2.0 | 28.3 ± 1.4 | 31.5 ± 2.8 |
| fast wave sleep stage | 0-3 | 6.0 ± 1.7 | 5.5 ± 1.6 | 2.7 ± 0.9 | 3.2 ± 1.7 |
|  | 4-6 | 11.5 ± 1.3 | 13.4 ± 2.1 | 2.4 ± 0.4 | 3.0 ± 0.7 |

TABLE 13

Latency time (unit: min) of each sleep stage after administration

| sleep - wake cycle | Light period | | Dark period | |
|---|---|---|---|---|
|  | control group | glycine group | control group | glycine group |
| slow wave sleep stage | 22.1 ± 9 | 8.5 ± 1.2 | 73.0 ± 13.4 | 78.6 ± 22.8 |
| fast wave sleep stage | 20.4 ± 6 | 20.9 ± 3.4 | 99.6 ± 34.6 | 118.2 ± 28.3 |

TABLE 14

Amount (unit: count) of spontaneous motor activity at 6 hr after administration

|  | control group | glycine group |
|---|---|---|
| light period | 4193 ± 777 | 2316 ± 295 |
| dark period | 21519 ± 2997 | 19464 ± 2765 |

When glycine was administered during the daytime, the proportion of waking stage became less as compared to the control. As to the detail of the sleep stage, both the slow wave sleep stage and the fast wave sleep stage slightly increased. In contrast, the dark period did not show any effect. As shown in Table 13, for each latency time of the sleep stage, namely, the time before the first emergence of sleep after administration, the slow wave sleep stage latency time was shortened in the glycine administration group and it was suggested that a deep sleep might have been easily induced by glycine.

As shown in Table 14, moreover, the amount of spontaneous motor activity during the light period decreased in the glycine administration group, but it did not show any difference in the dark period. From the above results, it was shown that glycine encourages natural sleep without markedly changing the constitution of sleep only in the light period, which is the inherent resting stage of rats.

Experimental Example 12

A single-blind crossover study aimed at confirmation of the effect of glycine on sleep was performed with 7 male adults (30s-40s, body weight 62-79 kg). The test participants took glycine (granule containing citric acid and the like) in an amount equivalent to 3 g of glycine 30 min before bedtime, and reduced maltose containing components other than glycine (citric acid and the like) and adjusted to an almost indistinguishable taste was used as a placebo. The sleep hours on the day of administration was limited to about 75% (5-6.5 hr) of comfortable sleep hours each test participant voluntarily notified, and a nap was prohibited until the end of the administration. For the test, glycine and placebo were each taken for 3 days with an interval of a 14-21 day non-intake period, totaling 4-5 weeks. Of the 3 days, the following investigation and measurement were performed at 10 o'clock, 14 o'clock and 18 o'clock of the next day of the first day of the intake.

(1) As a result of examination using self recording questionnaire for the evaluation of physical and mental conditions, an effect of significantly improving physical and mental conditions such as daytime lassitude and sleepiness was observed, as shown in Table 15. In the Table, the values of glycine and placebo regarding "lassitude" show the total points of 10 questions (each 3 levels of 0, 1, 2 points) evaluating the lassitude in a SAM lassitude check list. A greater value means that greater lassitude was felt. The values of glycine and placebo regarding "sleepiness" show the distance from the left end, wherein the left end of a 100 mm line is "no sleepiness" and the right end is "very sleepy", and the condition from the feeling at that time was marked on the line. A greater value means that the sleepiness was intense. In addition, the p value is a statistical value showing the probability when the difference between glycine and placebo was hypothesized to be null. Particularly, this value of 0.05 or below is considered to indicate a significant difference. It was shown that glycine improved physical and mental conditions such as daytime lassitude and sleepiness of the next day by improving the sleep conditions.

(2) To evaluate the cognitive and psychomotor function as a reflection of the quality of sleep, an operation efficiency test using a computer was performed. The results are shown in Table 16. As a three kind discrimination response task, a task of responding to only one predetermined kind from randomly designed three kinds of graphics on the screen was given. As a result, increase in the percentage of correct answer, shortened response time, and decrease in lapse (number of response where reaction time was 500 msec or longer) were significantly observed. From these results, it was shown that glycine increased psychomotor function during the next daytime and improved operation efficiency and concentration by increasing the quality of sleep.

TABLE 15

Effect of decreasing lassitude of next daytime by glycine intake

|  | Placebo (mean ± standard error) | Glycine (mean ± standard error) | p value |
|---|---|---|---|
| lassitude | 9.0 ± 0.68 | 7.0 ± 0.74 | 0.025 |
| sleepiness | 50.7 ± 4.39 | 38.1 ± 4.47 | 0.042 |

TABLE 16

Effect of improving operation efficiency and concentration of next daytime by glycine intake

|  | Placebo (mean ± standard error) | Glycine (mean ± standard error) | p value |
|---|---|---|---|
| percentage of correct answer (%) | 95.6 ± 5.20 | 98.4 ± 1.16 | 0.043 |
| Response time (sec) | 0.393 ± 0.025 | 0.366 ± 0.021 | 0.028 |
| Lapse (times) | 2.67 ± 3.06 | 1.19 ± 1.69 | 0.017 |

INDUSTRIAL APPLICABILITY

The food of the present invention can provide a masking effect of an unpreferable flavor, a deep sleep disorder improving effect, such as an arousal during sleep suppressing effect and an early-morning awakening suppressing effect, a bowel movement improving effect and the like. A food of the type based on the unit intake of the present invention can easily enjoy the effect afforded by the above-mentioned action.

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A method of shortening slow wave sleep latency, comprising administering a composition comprising glycine to a human subject in need of such shortening, wherein the composition comprises 5 g or less of amino acids other than glycine.

2. The method of claim 1, wherein the composition comprises less than 50 mg of amino acids other than glycine.

3. The method of claim 1, wherein the composition comprises from 50 mg to less than 5 g of amino acids other than glycine.

4. The method of claim 1, wherein the composition is free of amino acids other than glycine.

5. The method of claim 1, wherein the composition is administered in an amount of 0.013 to 0.067 g/kg of body weight/day.

6. The method of claim 1, wherein administering the composition comprises administering at least 1.5 g of glycine in a single dose before bedtime.

7. The method of claim 1, wherein administering the composition comprises administering at least 3 g of glycine in a single dose before bedtime.

8. The method of claim 1, wherein the composition comprises glycine, a flavorant, and an additional excipient.

9. A method of extending the duration of slow wave sleep in early stage sleep, comprising administering a composition comprising glycine to a human subject in need of such extension, wherein the composition comprises 5 g or less of amino acids other than glycine.

10. The method of claim 9, wherein the composition comprises less than 50 mg of amino acids other than glycine.

11. The method of claim 9, wherein the composition comprises from 50 mg to less than 5 g of amino acids other than glycine.

12. The method of claim 9, wherein the composition is free of amino acids other than glycine.

13. The method of claim 9, wherein the composition is administered in an amount of 0.013 to 0.067 g/kg of body weight/day.

14. The method of claim 9, wherein administering the composition comprises administering at least 1.5 g of glycine in a single dose before bedtime.

15. The method of claim 9, wherein administering the composition comprises administering at least 3 g of glycine in a single dose before bedtime.

16. The method of claim 9, wherein the composition comprises glycine, a flavorant, and an additional excipient.

* * * * *

UNITED STATES PATENT AND TRADEMARK OFFICE
CERTIFICATE OF CORRECTION

PATENT NO. : 10,561,629 B2
APPLICATION NO. : 11/165200
DATED : February 18, 2020
INVENTOR(S) : Tohru Kouda et al.

Page 1 of 1

It is certified that error appears in the above-identified patent and that said Letters Patent is hereby corrected as shown below:

On the Title Page

Item (63), the Related U.S. Application Data is incorrect. Item (63) should read:
-- (63) Continuation-in-Part of Application No. PCT/JP2004/019771, filed on Dec. 24, 2004 --

Signed and Sealed this
Seventh Day of April, 2020

Andrei Iancu
*Director of the United States Patent and Trademark Office*